US008911997B2

(12) United States Patent
Upton et al.

(10) Patent No.: US 8,911,997 B2
(45) Date of Patent: Dec. 16, 2014

(54) MAMMALIAN CELL CULTURE MEDIUM

(75) Inventors: Zee Upton, Indooroopilly (AU); Damien Harkin, Forest Lake (AU); David Leavesley, Indooroopilly (AU)

(73) Assignee: Queensland University of Technology, Brisbane (AU)

( * ) Notice: Subject to any disclaimer, the term of this patent is extended or adjusted under 35 U.S.C. 154(b) by 1130 days.

(21) Appl. No.: 10/565,616

(22) PCT Filed: Jul. 28, 2004

(86) PCT No.: PCT/AU2004/001006
§ 371 (c)(1),
(2), (4) Date: Jun. 9, 2006

(87) PCT Pub. No.: WO2005/012508
PCT Pub. Date: Feb. 10, 2005

(65) Prior Publication Data
US 2006/0233764 A1    Oct. 19, 2006

(30) Foreign Application Priority Data

Jul. 28, 2003    (AU) ................................. 2003903896

(51) Int. Cl.
C12N 5/00          (2006.01)
C12N 5/071         (2010.01)
A61K 35/12         (2006.01)

(52) U.S. Cl.
CPC ............. *C12N 5/0629* (2013.01); *A61K 35/12* (2013.01); *C12N 2501/105* (2013.01)
USPC ........................................................ 435/405

(58) Field of Classification Search
USPC ........................................................ 435/405
See application file for complete search history.

(56) References Cited

U.S. PATENT DOCUMENTS

| 5,292,655 | A |   | 3/1994  | Wille, Jr. |            |
|-----------|---|---|---------|------------|------------|
| 5,360,789 | A | * | 11/1994 | Nakao et al. | 514/9.4  |
| 5,407,913 | A | * | 4/1995  | Sommer et al. | 514/12  |
| 5,830,504 | A | * | 11/1998 | Vuori et al. | 424/484  |
| 5,834,312 | A |   | 11/1998 | Wille, Jr. |            |

FOREIGN PATENT DOCUMENTS

| WO | WO 00/27996 A1  | 5/2000  |
| WO | WO 02/24219 A1  | 3/2002  |
| WO | WO-03/102134 A2 | 12/2003 |

OTHER PUBLICATIONS

Upton et al (Comparative Biochemistry and Physiology Part B, 121: 35-41, 1998).*
Nam et al (Endocrinology, 143(1): 30-36, 2002).*
Klemke et al, (The Journal of Cell Biology, 127: 859-866, 1994).*
Schvartz et al (The International Journal of Biochemistry & Cell Biology 31: 539-544, 1999).*
Onishi, T. et al., 1999, Stimulation of proliferation and differentiation of dog dental pulp cells in serum-free culture medium by insulin-like growth factor, *Archives of Oral Biology*, 44(4):361-371.
Chapinyo, K. et al., 2002, Effects of growth factor on cell proliferation and matrix synthesis of low-density, primary bovine chondrocytes cultured in collagen I gels, *Journal of Orthopaedic Research*, 20:1070-1078.
Nielsen, F. C. and Gammeltoft, S., 1988, Insulin-like growth factors are mitogens for rat pheochromocytoma PC 12 cells, *Biochemical and Biophysical Research Communications*, 154(3):1018-1023.
Hyde, C. et al., 2004, Insulin-like growth factors (IGF) and IGF-binding proteins bound to vitronectin enhance keratinocyte protein synthesis and migration, *Journal of Investigative Dermatology*, 122:1198-1206.
Schleicher et al., "Surface Modification by Complexes of Vitronectin and Growth Factors for Serum-Free Culture of Human Osteoblasts", *Tissue Engineering*, vol. 11, No. 11-12, Nov. 2005, pp. 1688-1698, XP-009072079.
Kricker et al., "Structural and Functional Evidence for the Interaction of Insulin-Like Growth Factors (IGFs) and IGF Binding Proteins with Vitronectin", *Endocrinology*, vol. 144, No. 7, Jul. 2003, pp. 2807-2815, XP-002398183.
Grant et al., "The Co-Application of Sprayed Cultured Autologous Keratinocytes and Autologous Fibrin Sealant in a Porcine Wound Model", *British Journal of Plastic Surgery*, vol. 55, No. 3, Apr. 2002, pp. 219-227, XP-002398188.
Nam et al., "Vitronectin Binding to IGF Binding Protein-5 (IGFBP-5) Alters IGFBP-5 Modulation of IGF-I Actions", *Endorinology*, vol. 143, No. 1, Jan. 2002, pp. 30-36.
Noble et al., 2003 "Insulin-Like Growth Factor-II Bound to Vitronectin Enhances MCF-7 Breast Cancer Cell Migration", *Endocrinology*, 144:2417-2424.
Kricker et al. 2003 "Structural and Functional Evidence for the Interaction of Insulin-Like Growth Factors (IGFs) and IGF Binding Proteins with Vitronectin", *Endocrinlogy*, 144:2807-2815.
Tsuboi et al. 1992 "Stimulation of Keratinocyte Migration by Growth Factors", *The Journal of Determatology*, 19:652-653.
O'Keefe et al. 1988 "Stimulation of Growth of Keratinocytes by Basic Fibroblast Growth Factor", *J. Invest. Dermatol*, 90:767-769.

(Continued)

*Primary Examiner* — Marcia S Noble
*Assistant Examiner* — Magdalene Sgagias
(74) *Attorney, Agent, or Firm* — Casimir Jones, S.C.

(57) ABSTRACT

A cell culture medium and system are provided which eliminate or at least reduce the requirement for exogenous components such as serum and feeder cells. The cell culture medium comprises an IGF and vitronectin or fibronectin and, optionally an IGFBP, and is particularly suitable for propagating keratinocytes for subsequent use in skin growth and regeneration. This invention also relates to compositions and methods for skin growth and regeneration in situ, which utilize aerosol delivery of cultured keratinocytes.

17 Claims, 6 Drawing Sheets

(56) References Cited

OTHER PUBLICATIONS

Figure 1:
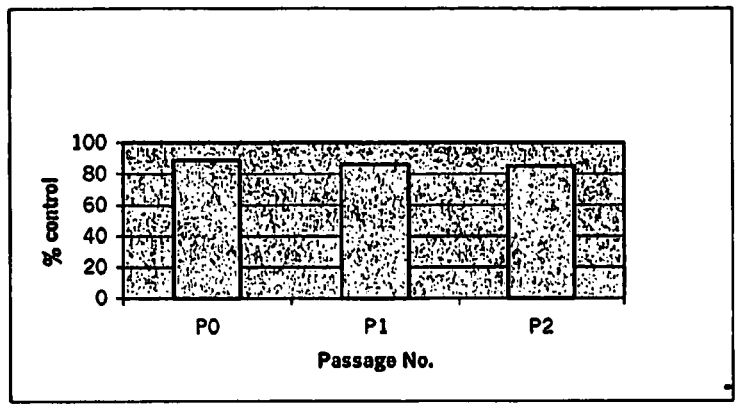

Ando et al. 1993 "Epidermal Growth Factor and Insulin-Like Growth Factor I Enhance Keratinocyte Migration", *J. Invest. Dermatol.*, 100:633-639.

Bhora et al., 1995, "Effect of Growth Factors on Cell Proliferation and Epithelialization in Human Skin", *J. Surg. Res.* 59:236-244.

Krane et al., 1991, "Synergistic Effects of Epidermal Growth Factor (EGF) and Insulin-Like Growth Factor I/Somatomedin C. (IGF-I) on Keratinocyte Proliferation May Be Mediated by IGF-I Transmodulation of the EGF Receiptor", *J. Invest. Dermatol*, 96:419-424.

Nam et al., 2002, "Vitronectin Binding to IGF Binding Protein-5 (IGFBP-5) Alters IGFBP-5 Modulation of IGF-I Actions", *Endocrinology*, 143:30-36.

Schleicher et al., 2005, "Surface Modification by Complexes of Vitronectin and Growth Factors for Serum-Free Culture of Human Osteoblasts", *Tissue Engineering*, 11:1688-1698.

Warwick et al., 2002, "The Co-Application of Sprayed Cultured Autologous Keratinocytes and Autologous Fibrin Sealant in a Porcine Wound Model", *British Journal of Plastic Surgery*, 55:219-227.

Nagano et al., 1992, "Yolk Vitronectin", *The Journal of Biological Chemistry*, 267:24863-24870.

Seger et al., 1998, "Phosphorylation of Vitronectin by Casein Kinase II", *The Journal of Biological Chemistry*, 273:24805-24813.

Ballard, "Regulation of Protein Accumulation in Cultured Cells", *Biochem J.*, (1982) 208, 275-287.

Francis et al., "Purification and Partial Sequence Analysis of Insulin-Like Growth Factor-1 From Bovine Colostrum", *Biochem. J.* (1986), 233, 207-213.

Upton et al., "Identification of Vitronectin as a Novel Insulin-Like Growth Factor-II Binding Protein", *Endocrinology* (1999) 140, 2928-2931.

\* cited by examiner a)

b)

MAMMALIAN CELL CULTURE MEDIUM

FIELD OF INVENTION

THIS INVENTION relates to cell culture. More particularly, this invention relates to a medium, system and method for propagating keratinocytes for subsequent use in skin growth and regeneration. This invention also relates to compositions for use in skin growth and regeneration in situ.

BACKGROUND OF THE INVENTION

The insulin-like growth factors (IGFs), IGF-I and IGF-II, are mitogenic peptide growth factors involved in a broad range of cellular processes including hyperplasia, DNA synthesis, differentiation, cell cycle progression and inhibition of apoptosis (Keiss et al., 1994, Hormone Research 41 66; Wood & Yee, 2000, J. Mammary Gland Biology and Neoplasia 5 1; Jones & Clemmons, 1995, Endocrine Rev. 16 3). These effects are mediated through binding to their tyrosine-kinase linked cell surface receptor, the type 1 IGF receptor (IGF-IR). The IGFs are also tightly regulated by a family of specific binding proteins, termed IGFBPs, whose primary role is to bind free IGFs and thereby moderate their half-life, specificity and activity (Clemmons, 1998, Mol. Cell. Endocrinol. 140 19).

Recently, vitronectin (VN) has been shown to bind directly to IGF-II (Upton et al., 1999. Endocrinology 140 2928-31) while IGF-I can bind to VN in the presence of certain IGFBPs (International Publication WO 02/24219; Kricker et al., 2003, Endocrinol. 144 2807-15). The finding that VN, an ECM organization and adhesion molecule, binds IGF-II with an affinity that is similar to that of IGF-II for IGF-IR (Upton et al., 1999, supra), its biologically relevant receptor, reveals a specific physical link between IGF action and VN in the ECM. In addition, IGF-II bound to VN, and IGF-I bound to VN via IGFBPs, can stimulate synergistic functional responses in a diverse range of cells including human keratinocytes in vitro (International Publication WO 02/24219; Noble et al., 2003, supra; Kricker et al., 2003, supra).

Wounds, burns and ulcers are debilitating and painful skin conditions that require intensive and costly treatments which, in many cases, are only partly successful. For example, more than 520,000 Australians are currently diagnosed with diabetes, and of these, more than 5% will experience foot ulcers. These wounds significantly compromise the quality of life of the patient, often lead to prolonged hospitalisation, and may ultimately result in amputation. In fact, the vast majority of lower limb amputations performed are attributed to a non-healing ulcer.

An increasingly preferred approach to healing wounds, burns and ulcers is to replace dead or damaged skin with autologous or allogeneic keratinocytes grown in vitro. Typically, keratinocytes are grown in defined media in the presence of exogenous factors such as serum or bovine pituitary extracts, usually with feeder cells that optimize keratinocyte growth.

SUMMARY OF THE INVENTION

Typical prior art its vitro cell culture systems are relatively expensive by virtue of the inclusion of the aforementioned exogenous factors. Furthermore, animal-derived exogenous factors such as serum and bovine pituitary extracts are relatively poorly defined and may harbour infectious agents such as those that cause CJD, HIV and other diseases.

To this end, the present inventors have discovered that protein complexes comprising IGF-II and VN or IGF-I and IGFBP and VN stimulate significant proliferative responses in primary cell cultures ex vivo in the absence of serum. More particularly, protein complexes comprising IGF-II and VN or IGF-I and IGFBP and VN can be used to enhance keratinocyte growth for the purposes of skin replacement, burn and wound healing and other therapeutic treatments that require skin growth ex vivo.

Therefore, in a first aspect, the invention provides a cell culture medium comprising:
  (i) at least an IGF selected from IGF-I and IGF-II; and
  (ii) an absence of serum or an amount of serum which in the absence of said at least an IGF would not support cell growth.

In one embodiment, the culture medium comprises IGF-I and an IGFBP.

In a second aspect, the invention provides a cell culture system comprising a culture vessel and the cell culture medium of the first aspect.

It will be appreciated that the culture medium and/or culture system of the invention may further comprise vitronectin (VN) and/or fibronectin (FN) or a fragment thereof.

In a third aspect, the invention provides a method of cell culture including the step of culturing one or more cells in the cell culture medium of the first aspect and/or the cell culture system of the second aspect.

In a fourth aspect, the invention provides a pharmaceutical composition comprising one or more cells produced cultured according to the method of the third aspect together with a pharmaceutically acceptable carrier, diluent or excipient.

In a preferred embodiment, the pharmaceutical composition is suitable for aerosol delivery of keratinocytes or keratinocyte progenitor cells.

In a fifth aspect, the invention provides a method of delivering keratinocytes or keratinocyte progenitor cells for skin regeneration in situ including the step of delivering the pharmaceutical composition of the fourth aspect to an individual to facilitate skin regeneration.

A preferred embodiment of this aspect provides a method of regenerating skin in situ, including the steps of:

(i) spraying one or more keratinocytes or keratinocyte progenitor cells onto the skin of an individual; and (ii) growing said keratinocytes or keratinocyte progenitor cells to form regenerated skin in situ.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE FIGURES

FIG. 1. Keratinocyte growth in the presence of isolated protein complexes and feeder cells in the absence of serum. The average growth of freshly isolated keratinocytes with VitroGro (+3t3 cells) relative to the conventional method where both foetal bovine serum and 3t3 cells are present. P0, P1 and P2 relative to the number of times that the cells have been harvested and replated (P0=performance of cells immediately following isolation from a skin sample). The data were obtained via staining with MTT which is converted to a coloured substrate by growing cells. Error bars are not shown owing to the large variation between different donor tissues.

FIG. 2. Keratinocyte morphology after growth in the presence of isolated protein complexes and feeder cells in the absence of serum. Cells were grown for 3 weeks in the presence of foetal bovine serum and mouse 3t3 cells (A) or grown for 3 weeks in the presence of VitroGro (B; vitronectin, IGFBP5 and IGF-I) and mouse 3t3 cells in the absence of serum. The scale bar is approximately 200 micrometers (μm).

Figure 3:
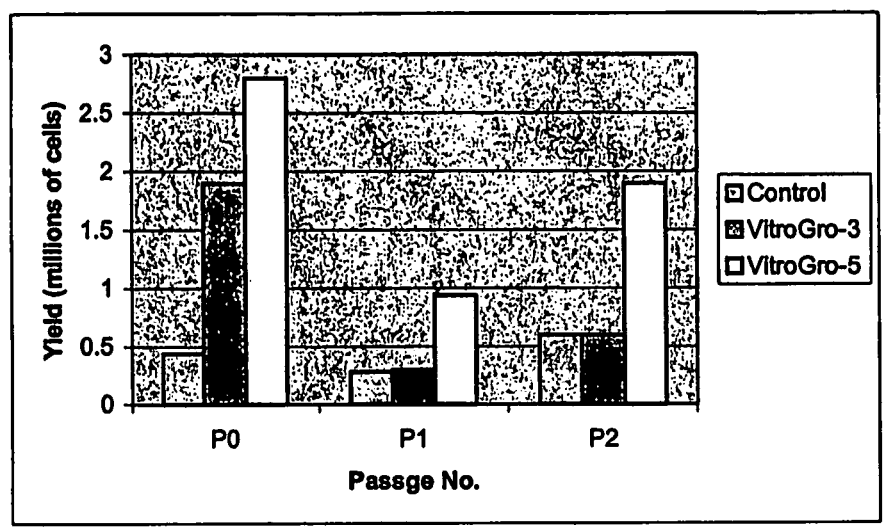

FIG. 3. Relative activity of isolated protein complexes containing IGFBP3 or IGFBP5. Control=standard keratinocyte growth medium supplemented with 10% foetal bovine serum. VitroGro-3=vitronectin, IGFBP3 and IGF-I (serum-free). VitroGro-5=vitronectin, IGFBP5 and IGF-I (serum-free). All cultures were grown in the presence of gamma irradiated mouse 3t3 cells.

Figure 4:
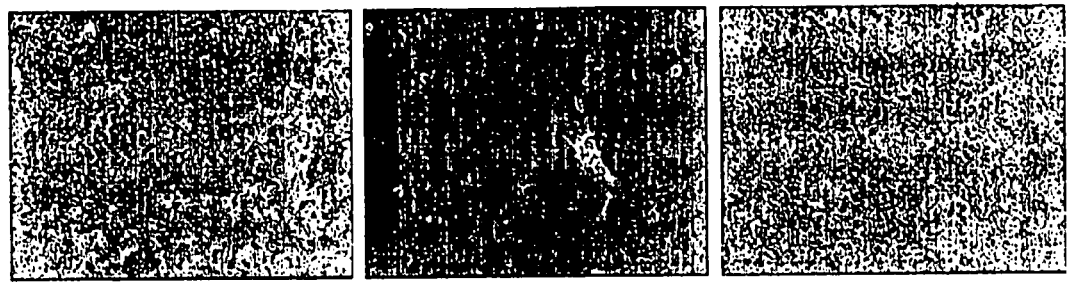
Figure 4:
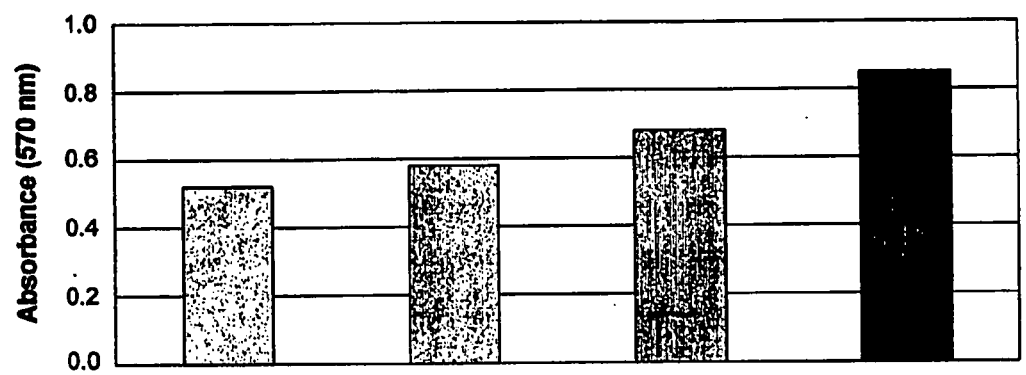

FIG. 4. IGF protein complexes support the ex vivo expansion of keratinocytes. Keratinocytes derived from adult human skin seeded onto IGF protein complexes survive and grow at rates comparable to cells seeded onto irradiated mouse 3T3 cells in the presence of fetal bovine serum. Cell growth was observed by: (a) visual examination of culture morphology/confluence; and (b) quantified by MTT assay. (a) from left to right: feeder layer+bovine serum; control without feeder layer or serum; IGF-I+IGFBP5+VN without feeder layer or serum; (b) left to right: Greens media+feeder layer+bovine serum; Greens media+feeder layer alone; Greens media−insulin+IGF-I, +IGFBP-3+VN; Greens media−insulin+IGF-I, +IGFBP-5+VN. VN is present at 300 ng/well. IGF-I or IGF-II are present at 100 ng/well and IGFBPs are present at 300 ng/well.

Figure 5:
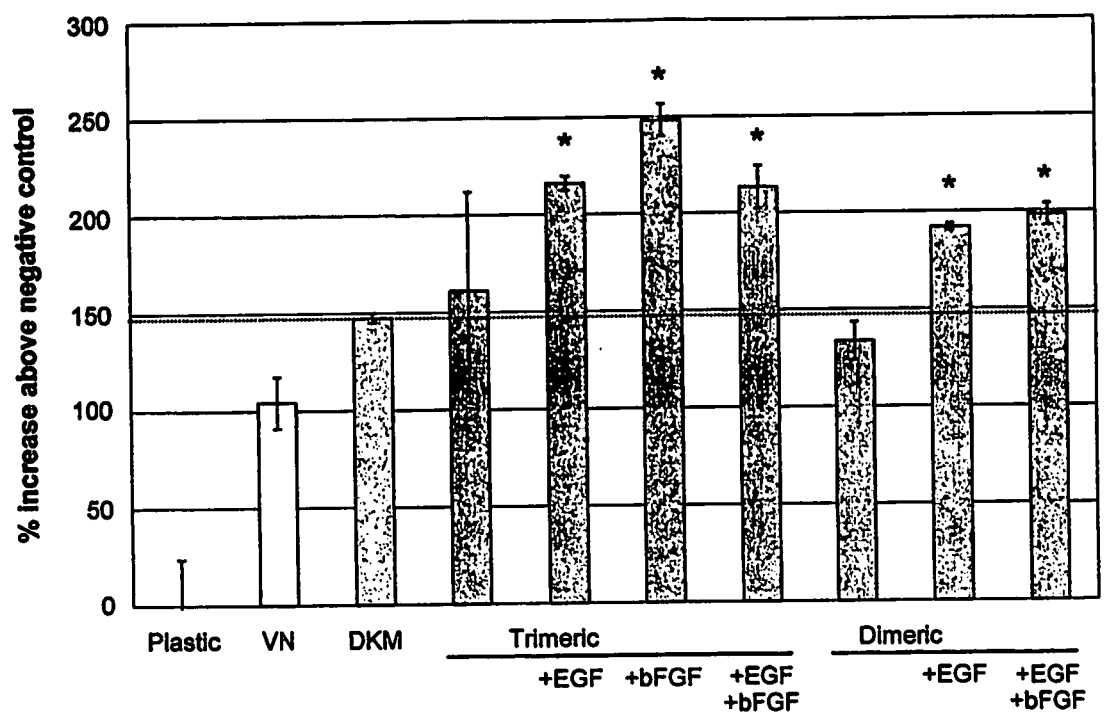

FIG. 5. IGF protein complexes supplemented with other growth factors further enhance growth of cultures of keratinocytes. Keratinocytes derived from adult human skin were cultured on IGF protein complexes plus epidermal growth factor (EGF) and basic fibroblast growth factor (bFGF) and assayed for protein synthesis by [$^3$H]-leucine incorporation. Cells seeded on trimeric IGF-I, IGFBP5 and VN or dimeric IGF-II and VN protein complexes grow at rates equivalent to Defined Keratinocyte Media (DKM, Invitrogen). IGF protein complexes further incorporating EGF (100 ng/well) and bFGF (100 ng/well) significantly enhanced protein synthesis compared to DKM ($p<0.05$). IGF-I or IGF-II are present at 100 ng/well, VN at 300 ng/well and IGFBPs are present at 300 ng/well.

Figure 6:
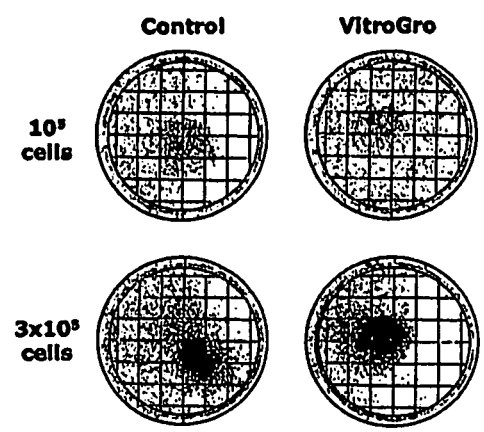

FIG. 6. Effect of TISSOMAT on keratinocyte viability. Cell distribution and growth following spray delivery of keratinocytes into 150 mm diameter collagen-coated cultures dishes. Cells were sprayed at two different concentrations to determine cell numbers required to cover sprayed area. The cultures used for spraying were originally grown on either control (with serum) or vitronectin with IGFBP3 and IGF-I (VitroGro). All cultures were prepared in presence of 3t3 cells. Cultures were then stained with crystal violet after 7 days growth on collagen coated plates in the presence of serum (designed to mimic conditions following delivery to wound bed). Spray volume was 0.2 ml, pressure 20 psi, height=10 cm.

Figure 7:
Figure 7:
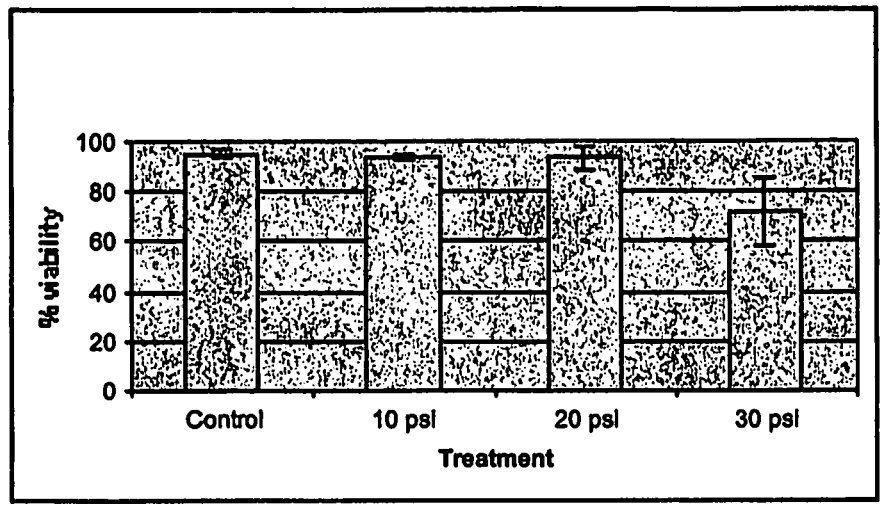
Figure 7:
Figure 7:
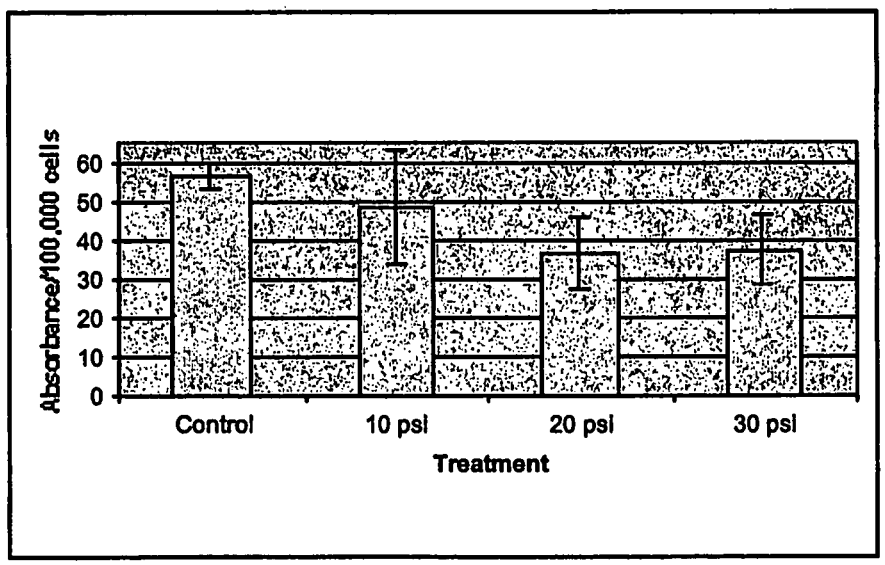

FIG. 7. Effect of TISSOMAT on keratinocyte viability. Cultures were established using the conventional culture medium with added serum. (A) The Trypan Blue exclusion test was performed within minutes following spraying cells into a collection tube. Viable cells are not permeable to the dye. (B) The MT conversion data is a measure of viability that provides an indication of the metabolic activity 24-hours after spraying the cells.

DETAILED DESCRIPTION OF THE INVENTION

The present invention has arisen from the discovery that culture media comprising IGF-II and VN or IGF-I and IGFBP and VN stimulate significant proliferative responses in primary cultures of keratinocytes ex vivo in the absence of serum, which is typically required for keratinocyte growth ex vivo.

Furthermore, the absolute requirement for feeder cells may be at least partly eliminated, particularly during later stages of cell culture after cell cultures have initially been established.

This invention therefore provides technology that improves current clinical best practice for ex vivo skin regeneration. In addition, the present invention also provides for the derivation and establishment of keratinocytes from tissue biopsies. In a preferred form, the invention provides a keratinocyte culture medium and system that utilizes autologous vitronectin isolated from a patient's own serum or produced recombinantly, thereby further minimizing the use of xenogeneic or allogeneic support systems, as well as eliminating use of poorly-defined supplementary products. This will therefore provide an autologous-cell based tissue engineering system that can be translated to approved therapeutic applications.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

As used herein, by "synthetic" is meant not naturally occurring but made through human technical intervention. In the context of synthetic proteins and nucleic acids, this encompasses molecules produced by recombinant or chemical synthetic and combinatorial techniques as are well understood in the art.

By "protein" is meant an amino acid polymer. The amino acids may be natural or non-natural amino acids, D- or L-amino acids as are well understood in the art.

A "peptide" is a protein having less than fifty (50) amino acids.

A "polypeptide" is a protein having fifty (50) or more amino acids.

In particular aspects, the invention provides a cell culture medium and system comprising at least IGF-I and/or IGF-II, such that exogenous, animal-derived factors such as serum are not required or are required at substantially reduced levels whereby cell growth and/or viability are maintained.

It will be appreciated that the invention is applicable to any mammalian cell type that is responsive to IGF-I and/or IGF-II.

Generally, such cells are mesoderm-derived cells such as epithelial cells, myoblasts and their progenitors, bone marrow and dendritic cells.

In a preferred embodiment, the invention is applicable to epithelial cells inclusive of skin epithelial cells such as keratinocytes, keratinocyte progenitors and corneal epithelial cells. Indeed, both skin and corneal epithelial cells may be regarded as "keratinocytes" since they produce keratin proteins.

Keratinocytes and/or their progenitors may be derived from normal skin, skin biopsies such as obtained from wounds or ulcers or from outer root sheath (ORS) cells of hair follicles, although without limitation thereto.

It will therefore be appreciated that the culture medium, method and system of the invention may potentially be used to engineer replacement tissues wherever epithelial cells are found e.g. the oral and respiratory mucosa (inner lining of mouth, nose, trachea and oesophagus) and genito-urinary tissue (e.g vagina, bladder). These tissues can also be damaged by burns and other trauma and as such can be treated using cultivated grafts grown in a similar way to the skin biopsies.

The invention may also be applicable to human embryonic stem (hES) cells, which also normally have a requirement for serum during culture.

It will therefore be appreciated that "an absence of serum or an amount of serum which in the absence of said at least an IGF would not support cell growth" means either no serum or a substantially reduced amount or concentration of serum than would ordinarily be required for optimal cell growth and/or development in vitro.

By "serum" is meant a fraction derived from blood that comprises a broad spectrum of macromolecules, carrier proteins for lipoid substances and trace elements, cell attachment and spreading factors, low molecular weight nutrients, and hormones and growth factors. Operationally, serum may be defined as the proteinaceous, acellular fraction of blood remaining after removal of red blood cells, platelets and clotted components of blood plasma. The most widely used animal serum for cell culture is fetal bovine serum, FBS, although adult bovine serum, horse serum and protein fractions of same (e.g. Fraction V serum albumin) may also be used.

Typically, mammalian cells require between 5-10% serum depending on cell type, duration of culture, the presence or absence of feeder cells and/or other cellular components of a culture system and other factors that are apparent to persons of skill in the art.

Thus, in a preferred embodiment, the invention contemplates less than 5% serum, more preferably less than 2% serum, even more preferably less than 1% serum or advantageously no more than 0.5%, 0.4%, 0.3% or 0.2% serum (v/v).

In particularly advantageous embodiments, the invention contemplates no serum or no more than 0.1%, or 0.05% serum (v/v).

In embodiments where IGF-I is present, it is preferred that IGF-I is a component of a protein complex Iuther comprising an IGFBP and vitronectin (VN).

The IGFBP is selected from IGFBP1, IGFBP2, IGFBP3, IGFBP4, IGFBP5 and IGFBP6.

Preferably, the IGFBP is IGFBP3 or IGFBP5.

More preferably, the IGFBP is IGFBP5.

In embodiments where IGF-II is present, it is preferred that IGF-II is a component of an isolated protein complex further comprising vitronectin (VN).

It will also be appreciated that vitronectin (VN) may be in monomeric or multimeric form.

In one particular embodiment, the invention comprises autologous, purified VN.

Preferably, keratinocytes are cultured in culture vessels as typically used in the art. It will therefore be appreciated that the respective amounts of IGFs, VN and IGFBPs present during culture will depend on factors such as the size of the culture vessel, amount of liquid medium present in the vessel, cell density and other factors known in the art.

For guidance, in a 1.9 cm$^2$ well, preferred amounts are as follows:

VN: 50-5000 ng, more preferably 100-500 ng or advantageously 250-350 ng;

IGF: 0.1 to 1000 ng, more preferably 10-200 ng or advantageously 50-150 ng; and

IGFBP: 1 to 1000 ng, more preferably 30-700 ng or advantageously 300-500 ng.

Suitably, the culture medium of the invention comprises other defined components. Non-limiting and in some cases optional components include well known basal media such as DMEM or Ham's media, antibiotics such as streptomycin or penicillin, human serum albumin (HSA), phospholipids (eg. phosphatidylcholine), amino acid supplements such as L-glutamine, anti-oxidants such as β-mercaptoethanol, transferrin, buffers such as carbonate buffers, HEPES and a source of carbon dioxide as typically provided by cell culture incubators.

The invention also contemplates use of additional biologically active proteins that regulate cell growth, differentiation, survival and/or migration such as epidermal growth factor (EGF; Heldin et al., 1981, Science 4 1122-1123), fibroblast growth factor (FGF; Nurcombe et al., 2000, J. Biol. Chem. 275 30009-30018), basic fibroblast growth factor (bFGF; Taraboletti et al., 1997, Cell Growth. Differ. 8 471-479), osteopontin (Nam et al., 2000, Endocrinol. 141 1100), thrombospondin-1 (Nam et al., 2000, supra), tenascin-C (Arai et al., 1996, J. Biol. Chem. 271 6099), PAI-1 (Nam et al., 1997, Endocrinol. 138 2972), plasminogen (Campbell et al., 1998, Am. J. Physiol. 275 E321), fibrinogen (Campbell et al., 1999, J. Biol. Chem 274 30215), fibrin (Campbell et al., 1999, supra) or transferrin (Weinzimer et al., 2001, J. Clin. Endocrinol. Metab. 86 1806).

Preferred additional biologically active proteins are EGF and bFGF.

Additional biologically active proteins such as EGF and bFGF may be present at 0.1 to 1000 ng or advantageously 1-100 ng per 1.9 cm$^2$ culture well.

In a particular embodiment, the invention contemplates use of any growth factor with a heparin-binding-like domain.

In another particular embodiment, the invention contemplates use of LIF and/or other agents that inhibit cell differentiation in addition to isolated protein complexes.

In yet another particular embodiment, the invention contemplates use of one or more of poly-L-lysine and poly-L-arginine and secreted cellular material that interacts with vitronectin, for example polymers of collagens, fibronectins, glycosaminoglycans/proteoglycans, laminins, sialoproteins and/or mucins in the culture medium, system and/or method of the invention.

It is also proposed that the invention may facilitate cell culture in the absence of feeder cells, at least after the initial establishment stages of cell culture.

In the context of keratinocytes and/or keratinocyte progenitors, feeder cells (such as irradiated 3t3 feeder cells) may be present for the initial 6-7 days of culture in the absence of serum, after which time feeder cells may be absent for up to two passages.

In light of the foregoing and although not wishing to be bound by any particular theory, it is proposed that IGF-I forms an isolated protein complex with an IGFBP and VN while IGF-II forms a complex with VN to exert a biological effect during cell culture.

The term "isolated protein complex" is used herein consistent with that used in International Publication WO 02/24219 and International. Application PCT/AU2004/000117.

Isolated protein complexes may be pre-formed and included in the culture medium of the invention or may form in the culture vessel.

Typically, vitronectin and/or fibronectin are bound, immobilized, coated or otherwise associated with the culture vessel. Addition of an IGF and, optionally, an IGFBP, forms a complex with the vitronectin and/or fibronectin bound, immobilized, coated or otherwise associated with the culture vessel.

As described in International Application PCT/AU2004/000117, isolated protein complexes of the invention may comprise a growth factor (e.g. IGF-I and IGF-II), or at least a domain of a growth factor which is capable of binding a cognate growth factor receptor (e.g. IGF type 1 receptor).

In this context, by "domain" is meant at least that portion or region of a growth factor that is capable of binding a cognate growth factor receptor. Typically, although not exclusively, the cognate growth factor receptor is expressed by a cell and binding or ligation of said cognate growth factor receptor by said at least a domain of a growth factor elicits a cellular response such as cell growth, differentiation, survival and/or migration.

With particular regard to IGF-I, said domain suitably comprises amino acid residue 24, which is not a leucine residue.

Typically, said residue is tyrosine.

With particular regard to IGF-II, said domain suitably comprises amino acid residue 27, which is not a leucine residue.

Typically, said residue is tyrosine.

With particular regard to IGF-I, in one embodiment said domain comprises or consists of residues 1 to 70 of IGF-I.

In another embodiment, said domain comprises or consists of residues 4 to 70 of IGF-I.

It will also be understood that another component of isolated protein complexes of the invention is at least an integrin-binding domain of vitronectin or fibronectin.

This includes and encompasses any domain of VN or FN which is capable of binding an $\alpha_v$ integrin.

More preferably, the integrin is an $\alpha_v\beta_3$ integrin or an $\alpha_v\beta_5$ integrin.

As described in International Application PCT/AU2004/000117, the heparin binding domain (HBD) of VN (and analagously FN) is not required for the full biological activity of isolated protein complexes.

With regard to VN, it is most likely the polyanionic region of VN (and analagously FN) that is required for interaction with IGF-II or IGF-I/IGFBP complexes.

The polyanionic region is amino acid residues 53-64 of the mature VN sequence.

In light of the foregoing, the present invention contemplates embodiments of synthetic chimeric proteins that do not include the HBD and/or the polyanionic region of VN or FN.

With regard to VN proteins and amino acid sequences thereof that do not include the HBD and/or the polyanionic region, these may be naturally occurring proteins such as the 54 kDa chicken yolk VN (lacking a HBD) or may be engineered by deletion, mutation or truncation of a VN protein or amino acid sequence so that the HBD and/or the polyanionic region are absent or at least substantially non-functional.

It will be readily appreciated from the foregoing that isolated protein complexes of the invention may be in the form of non-covalently associated oligo-protein complexes, oligo-protein complexes that have been covalently cross-linked (reversibly or irreversibly) or in the form of synthetic, chimeric proteins.

Accordingly, in a particular aspect the invention provides an isolated protein complex in the form of a synthetic chimeric protein.

As used herein, a "chimeric protein", comprises a contiguous sequence of amino acids derived from an integrin-receptor binding domain of VN or FN and a growth factor or at least a receptor-binding domain of a growth factor.

Although not wishing to be bound by any particular theory, it is proposed that synthetic chimeric proteins may be able to co-ligate and co-activate a cognate receptor for said growth factor and an integrin receptor for VN or FN to thereby stimulate, induce, augment or otherwise promote cell migration.

An advantage of chimeric proteins according to the invention is that they are readily produced by chemical synthetic or recombinant means and are expected to be more stable in vivo, as they do not rely on maintaining the protein-protein interactions that are required in non-covalent oligo-protein complexes.

In this regard, although isolated protein complexes that comprise receptor binding domains of IGF-I would also comprise an IGFBP, it is proposed that according to the aforementioned mode of action, an IGFBP is preferably not present in an IGF-I/VN synthetic chimera.

Preferably, chimeric proteins further comprise a "linker sequence" located between and contiguous with a growth factor sequence and a VN or FN amino acid sequence.

In one embodiment, said linker sequence comprises one or more glycine residues and one or more serine residues.

Particular examples of linker sequences may be selected from; $Gly_4$ Ser; $Gly_4$ $Ser_3$ and $(Gly_4 Ser)_3$, although without limitation thereto.

In another embodiment, the linker sequence includes a Plasmin Cleavage Recognition Site, such as according to the sequence:

Leu Ile Lys Met Lys Pro

In yet another embodiment, the linker sequence includes a Collagenase-3 Cleavage Recognition Site, such as according to the sequence:

Gln Pro Gln Gly Leu Ala Lys

The aforementioned are examples of biologically-active fragments of a growth factor, growth factor binding protein and/or vitronectin/fibronectin.

In one embodiment, said "biologically-active fragment" has no less than 10%, preferably no less than 25%, more preferably no less than 50% and even more preferably no less than 75%, 80%, 85%, 90% or at least 95% of a biological activity of a "full length" protein.

Also contemplated are variant growth factors, growth factor binding proteins and/or vitronectin/fibronectin. and/or encoding nucleic acids that may be used according to the invention.

In one embodiment, a "variant" has one or more amino acids that have been replaced by different amino acids. It is well understood in the art that some amino acids may be changed to others with broadly similar properties without changing the nature of the activity of the protein (conservative substitutions).

In one embodiment, a variant shares at least 70%, preferably at least 80%, more preferably at least 90% and advantageously at least 95%, 96%, 97%, 98% or 99% sequence identity with the amino acid sequences described herein.

Preferably, sequence identify is measured over at least 60%, more preferably at least 75%, even more preferably at least 90% and advantageously over substantially the full length of the synthetic protein of the invention.

In order to determine percent sequence identity, optimal alignment of amino acid and/or nucleotide sequences may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference.

In another example, "sequence identity" may be understood to mean the "match percentage" calculated by the DNASIS computer program (Version 2.5 for windows; available from Hitachi Software engineering Co., Ltd., South San Francisco, Calif., USA).

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The invention also contemplates derivatives of a growth factor, growth factor binding protein and/or vitronectin/fibronectin.

As used herein, "derivative" has been altered, for example by addition, conjugation or complexing with other chemical moieties or by post-translational modification techniques as are well understood in the art "Additions" of amino acids may include fusion with other peptides or polypeptides. The other peptide or polypeptide may, by way of example, assist in the purification of the protein. For instance, these include a polyhistidine tag, maltose binding protein, green fluorescent protein (GFP), Protein A or glutathione S-transferase (GST).

Other derivatives contemplated by the invention include, but are not limited to, modification to side chains, incorporation of unnatural amino acids and/or their derivatives during protein synthesis and the use of crosslinkers and other methods which impose conformational constraints on proteins. Non-limiting examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

The imidazole ring of a histidine residue may be modified by N-carbethoxylation with diethylpyrocarbonate or by alkylation with iodoacetic acid derivatives.

Examples of incorporating non-natural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Further examples of chemical derivatization of proteins are provided in Chapter 15 of CURRENT PROTOCOLS IN PROTEIN SCIENCE Eds. Coligan et. al., John Wiley & Sons NY (1995-2001).

According to the invention, a protein may be prepared by any suitable procedure known to those of skill in the art.

In one embodiment, proteins may be in substantially pure native form.

One particular example is purified autologous vitronectin.

In another embodiment, a protein may be produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2001) for examples of suitable methodology.

In yet another embodiment, a protein may be prepared as a recombinant protein.

Production of recombinant proteins is well known in the art, the skilled person may refer to standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

Recombinant proteins may further comprise a fusion partner.

Well known examples of fusion partners include, but are not limited to, glutathione-S-transferase (GST), Fc portion of human IgG, maltose binding protein (MBP) and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

In some cases, the fusion partners also have protease cleavage sites, such as for Factor $X_a$ or Thrombin, which allow the relevant protease to partially digest the fusion protein of the invention and thereby liberate the recombinant protein therefrom. The liberated protein can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Suitable host cells for expression may be prokaryotic or eukaryotic, such as *Escherichia coli* (DH5α for example), yeast cells, Sf9 cells utilized with a baculovirus expression system, CHO cells, COS, CV-1, NIH 3T3 and HEK293 cells, although without limitation thereto.

The invention further contemplates use of cells, such as keratinocytes or keratinocyte progenitor cells, capable of expressing at least one recombinant protein selected from the group consisting of:

(i) a recombinant IGF;
(ii) a recombinant IGFBP;
(iii) a recombinant vitronectin;
(iv) a recombinant chimeric protein as hereinbefore described; and
(v) an additional biologically active protein such as EGF or bFGF.

According to a particular embodiment, paracrine/autocrine expression of IGFs, VN and/or IGFBPs may enable keratinocytes or keratinocyte progenitors to be cultured in media without serum and without the need to add one or more of growth factors, IGFBPs and/or vitronectin to the culture medium.

Recombinant protein expression may be achieved by introduction of an expression construct into a keratinocyte or keratinocyte progenitor cell.

Typically, the expression construct comprises a nucleic acid to be expressed (encoding the recombinant protein) operably linked or operably connected to a promoter.

The promoter may be constitutive or inducible.

Constitutive or inducible promoters include, for example, tetracycline-repressible, ecdysone-inducible, alcohol-inducible and metallothionin-inducible promoters. Promoters may be either naturally occurring promoters (e.g. alpha crystallin promoter, ADH promoter, phosphoglycerate kinase (PGK), human elongation factor α promoter and viral promoters such as SV40, CMV, HTLV-derived promoters), or synthetic hybrid promoters that combine elements of more than one promoter (e.g. SR alpha promoter).

In a preferred embodiment, the expression vector comprises a selectable marker gene. Selectable markers are useful whether for the purposes of selection of transformed bacteria (such as bla, kanR and tetR) or transformed mammalian cells (such as hygromycin, G418 and puromycin).

Expression constructs may be introduced into mammalian cells such as keratinocyte or keratinocyte progenitor cells by well known means such as electroporation, microparticle bombardment, virus-mediated gene transfer, calcium phosphate precipitation, DEAE-Dextran, cationic liposomes, lipofectin, lipofectamine and the like, although without limitation thereto.

For non-limiting particular examples of methodology potentially applicable to expression of recombinant growth factor proteins in keratinocytes, reference may be made to Supp et al., 2000, J. Invest. Dermatol. 114 5 and Supp et al., 2000, Wound Repair Regen. 8 26-35.

Pharmaceutical Compositions

The invention also provides pharmaceutical compositions that comprise on or more cells produced using the culture medium and/or system of the invention, such as keratinocytes although not limited thereto, together with a pharmaceutically acceptable carrier diluent or excipient.

Pharmaceutical compositions of the invention may be used to promote or otherwise facilitate cell migration, tissue regeneration and wound healing.

Generally, the compositions of the invention may be used in therapeutic or prophylactic treatments as required. For example, pharmaceutical compositions may be applied in the form of therapeutic or cosmetic preparations for skin repair, wound healing, healing of burns and other dermatological treatments.

Preferably, the pharmaceutically-acceptable carrier, diluent or excipient is suitable for administration to mammals, and preferably, to humans.

In particular embodiments, the pharmaceutical composition comprises autologous or allogeneic keratinocytes cultured according to the invention.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion.

Controlled release formulations may be effected by coating, for example, with hydrophobic polymers including acrylic resins, waxes, higher aliphatic alcohols, polylactic and polyglycolic acids and certain cellulose derivatives such as hydroxypropylmethyl cellulose. Controlled release may be effected by using other polymer matrices, liposomes and/or microspheres. Non-limiting examples of controlled release formulations and delivery devices include osmotic pumps, polylactide-co-glycolide (PLG) polymer-based microspheres, hydrogel-based polymers, chemically-crosslinked dextran gels such as OctoDEX™ and dex-lactate-HEMA, for example.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

With regard to pharmaceutical compositions for wound healing, particular reference is made to U.S. Pat. No. 5,936, 064 and International Publication WO99/62536 which are incorporated herein by reference.

In one particular embodiment, the composition of the invention is suitable for spray delivery in situ.

The term "spray" encompasses and includes terms such as "aerosol" or "mist" or "condensate" that generally describe liquid suspensions in the form of droplets.

According to the invention, although optional, the spray or aerosol composition may further comprise at least an IGF selected from IGF-I and IGF-II, or in particular embodiments, isolated protein complexes comprising IGFs, VN and IGFBPs, to promote skin cell growth and migration in situ. Additional biologically active proteins such as EGF and/or bFGF may also be included.

Although not wishing to be bound by any particular theory, the invention contemplates that the inherent "stickiness" of VN in IGF complexes present in the spray composition will facilitate delivery of IGF-I, IGF-II and other growth factors such as EGF and bFGF.

Typically, spray compositions of the invention will be delivered by apparatus such as a pressurised canister equipped with a delivery outlet.

An example of an aerosolised keratinocyte delivery systems such as for wound healing in a pig model, is provided by Navarro et al., 2000, J Burn Care Rehabil 21 513. Reference is also made to Grant et al., 2002, Br J Plast Surg 55 219 which describes use of aerosolised keratinocytes in conjunction with fibrin glue for wound healing in a pig model.

Preferably, spray compositions of the invention are substantially free of serum.

In one particular embodiment, the skin spray composition of the invention comprises Tissomat® (Baxter Healthcare), which facilitates spray-application of fibrin glue and aerosolises liquids via delivery into a stream of compressed medical grade air controlled by a regulator. Pressures of between 10-30 psi are suitable, but a drop in viability is observed within increasing pressure. Cells may be sprayed at concentrations of between 0.5 to 1.5 million per milliliter. Application of 0.2 milliliters of cell suspension at 20 psi is sufficient to cover an area of approximately 25 square centimeters (based on measurement of surface area covered with cells after 7 days growth in vitro). Cells are preferably delivered in serum free growth medium, but may also be suspended in fibrin glue such as the commercially available Tisseel/Tissucol (Baxter Healthcare).

It is also contemplated that similar efficacy may be achieved using syringe delivery of composition of the invention (e.g. a syringe fitted with a spray cap).

Therapeutic Uses

In particular aspects, the present invention provides methods of treating burns, wounds and ulcers as well as methods that relate to cosmetic skin treatments to improve or enhance skin quality or skin appearance.

These methods are particularly aimed at treatment of mammals, and more particularly, humans. However, it will also be appreciated that the invention may have veterinary applications for treating domestic animals, livestock and performance animals as would be well understood by the skilled person.

In a preferred embodiment, the invention provides a culture medium, system and method for propagating primary keratinocytes ex vivo, which cells may be administered to an individual according to the invention.

In particular embodiments, the keratinocytes are autologous or allogeneic keratinocytes cultured according to the invention.

Such methods include administration of pharmaceutical compositions as hereinbefore defined, and may be by way of microneedle injection into specific tissue sites, such as described in U.S. Pat. No. 6,090,790, topical creams, lotions or sealant dressings applied to wounds, burns or ulcers, such as described in U.S. Pat. No. 6,054,122 or implants which release the composition such as described in International Publication WO99/47070.

There also exist methods by which skin cells can be genetically modified for the purpose of creating skin substitutes, such as by genetically engineering desired growth factor expression (Supp et al., 2000, J. Invest. Dermatol. 114 5). An example of a review of this field is provided in Bevan et al., Biotechnol. Gent. Eng. Rev. 16 231.

Also contemplated is "seeding" a recipient with transfected or transformed cells, such as described in International Publication WO99/11789.

These methods can be used to stimulate cell migration and thereby facilitate or progress wound and burn healing, repair of skin lesions such as ulcers, tissue replacement and grafting such as by in vitro culturing of autologous skin, re-epithelialization of internal organs such as kidney and lung and repair of damaged nerve tissue.

Skin replacement therapy has become well known in the art, and may employ use of co-cultured epithelial/keratinocyte cell lines, for example as described in Kehe et al., 1999, Arch. Dermatol. Res. 291 600 or in vitro culture of primary (usually autologous) epidermal, dermal and/or keratinocyte cells. These techniques may also utilize engineered biomaterials and synthetic polymer "scaffolds".

Examples of reviews of the field in general are provided in Terskikh & Vasiliev, 1999, Int. Rev. Cytol. 188 41 and Eaglestein & Falanga, 1998, Cutis 62 1.

More particularly, the production of replacement oral mucosa useful in craniofacial surgery is described in Izumi et al., 2000, J. Dent. Res. 79 798. Fetal keratinocytes and dermal fibroblasts can be expanded in vitro to produce skin for grafting to treat skin lesions, such as described in Fauza et al., J. Pediatr. Surg. 33 357, while skin substitutes from dermal and epidermal skin elements cultured in vitro on hyaluronic acid-derived biomaterials have been shown to be potentially useful in the treatment of burns (Zacchi et al., 1998, J. Biomed. Mater. Res. 40 187).

Polymer scaffolds are also contemplated for the purpose of facilitating replacement skin engineering, as for example described in Sheridan et al., 2000, J. Control Release 14 91 and Fauza et al., 1998, supra, as are microspheres as agents for the delivery of skin cells to wounds and burns (LaFrance & Armstrong, 1999, Tissue Eng. 5 153).

Keratinocyte sheets typically produced for therapeutic use are responsible for the ultimate closure of burn wounds. This sheet graft technique is applicable to all partial thickness burn injuries and is most useful in treating large surface area wounds where early permanent closure of both wound and donor sites is nearly impossible without external help. This is the type of injury responsible for the death of patients burnt in the recent Bali bombing.

Currently, it is possible to grow enough skin from a patient skin biopsy the size of a fifty-cent piece to cover an entire adult. This culture process takes 17 days.

However, earlier skin replacement is urgently needed to reduce patient trauma, risk of infection, scarring and the present requirement for expensive temporary skin replacements ahead of permanent skin grafting. In addition, a sheet of cultured skin comprises many skin cells, some mature and some immature. The simple act of allowing cultured keratinocytes to reach confluence (necessary to produce sheets of skin) causes cells to prematurely loose their primitive characteristics i.e to differentiate. When a sheet of cultured skin is applied, only the immature cells are capable of attaching and establishing themselves on the patient. Because only small areas adhere, the sheets are very susceptible to damage arising from friction or movement of the patient and can sometimes result in the loss of the entire graft. Furthermore, in a sheet graft, the more mature skin cells in the sheet, the more likely it will be that the graft will not take and the cells themselves will not proliferate and migrate on the wound bed itself. Thus it is clear that earlier application of immature skin cells will result in better graft take and reduce scarring.

The present invention therefore provides a spray or aerosol delivery method to deliver skin cells cultured ex vivo onto a patient's burnt, ulcerated or wounded skin to enable a larger surface area of the patient's body to be covered by immature skin cells much earlier than existing sheet graft technology. This could be as early as only 7 days. This would also significantly reduce scar formation, shock and heat loss and would enable faster return of skin function in partial thickness and also full thickness burns.

According to the invention, although optional, the administered spray or aerosol may further comprise isolated protein complexes comprising IGFs, VN and IGFBPs together EGF and/or bFGF to promote skin cell growth and migration in situ.

The patients' own skin cells (autologous skin) and donor skin cells (allogeneic or heterologous skin) can be grown and used for early burn closure. Donor cells do not express transplantation antigens, so they do not cause an immune response in the patient. The donor skins cells, however, are eventually replaced by the patients' own skin cells.

Although autologous cells are preferred, use of allogeneic or heterologous cells in a spray-on-skin would allow immediate application to a needy patient. Alternatively, sufficient autologous skin cells could be cultured in approximately seven days for use in a therapeutic spray.

Another treatment contemplated by the present invention is the treatment of burns patients to achieve early closure of full thickness wounds, because take of cultured skin on a wound that has removed both the surface (epidermal) and deep layer (dermis) of skin is poor. The invention contemplates use of dermal substitutes in conjunction with the spray-on-skin to effect early permanent closure of these most horrific injuries. Both biological and synthetic dermal substitutes are contemplated. For example, a de-epidermised, de-cellularised cadaveric-derived dermal scaffold comprising isolated protein complexes of the invention may be overlayed with a synthetic epidermis (dressing). After approximately 7 days the dermis the present inventors hypothesise that this dermis will be highly infiltrated by autologous endothelial cells. At this time, the synthetic dermis will be removed and the patient's own ex-vivo expanded fibroblasts and keratinocytes will be applied to the allodermis.

It is anticipated that the spray-on-skin, rather than epidermal sheets, will be successful as the dermal substitute will act as a nutritious stabilising scaffold promoting the migration and anchoring of skin cells and other important cells normally found in the skin. This will result in improved take of cultured skin cells in full thickness skin injuries So that the present invention may be more readily understood and put into practical effect, the skilled person is referred to the following non-limiting examples.

EXAMPLES

Example 1

Primary Human Keratinocyte Growth in an Absence of Serum

Materials and Methods

Growth Factor Concentrations/Pre-Absorption to Culture Plastic

A standard approach for adding VN, IGF and IGFBP has been used throughout all studies. Culture plastic is prepared by incubating for 2 hours at 37 degrees C with vitronectin 150 ng/cm$^2$ in serum-free culture medium. The VN solution is then removed and replaced with serum-free medium containing IGFBP (250 ng/cm$^2$), IGF-I (50 ng/cm$^2$) and EGF (50 ng/cm$^2$). The growth factors are left over night at 4 degrees C. (in the fridge) to absorb to the VN treated plastic. The following day, the growth factor solution is removed and replaced with growth medium (defined below) containing 50 ng/ml VN, 50 ng/ml IGFBP, 15 ng/cm IGF-I and 15 ng/cm EGF. The cells are added at densities given below. The medium is typically changed once every 3 days. Each culture is grown for approximately 6 days before passaging: i.e. there are approximately 6 days between each passage.

Growth Medium

The base medium is a 3:1 mixture of Dulbecco's Modified Eagle's Medium (DMEM) with Ham's F12 medium that is routinely supplemented with L-glutamine (2 mM), cholera toxin (0.1 µg/ml), adenine (180 µM), hydrocortisone (0.4 µg/ml), and a mixture of non-essential amino acids (1% v/v).

Positive control medium contains an additional 10% fetal bovine serum, insulin (5 µg/ml) and epidermal growth factor (EGF, 10 ng/ml).

Seeding Densities

Cultures were grown in the presence of growth arrested mouse 3t3 cells at a density of $2.5 \times 10^4$/cm$^2$. The 3t3 cells are rendered "growth-arrested" by gamma irradiation immediately prior to use.

Keratinocytes were seeded at two different densities depending upon the passage number. Initial cultures (P0) were established by seeding cells at $3.8 \times 10^4$/cm$^2$. Subsequent cultures (P1, P2 etc) were established by re-seeding harvested cells at a density of $6.4 \times 10^3$/cm$^2$. The higher seeding density was used for the P0 cultures since only a fraction of the freshly harvested cells will display ongoing proliferation in culture. Thus, culturing the cells enables expansion of the proliferating subpopulation.

Results

Comparison of Cultures with Conventional Growth Medium Containing Serum.

Referring to FIG. 1, this graph displays the average growth of freshly isolated keratinocytes with VitroGro (+3t3 cells) relative to the conventional method where both foetal bovine serum and 3t3 cells are present. P0, P1 and P2 relative to the number of times that the cells have been harvested and replated (P0=performance of cells immediately following isolation from a skin sample). The data were obtained via staining with MTT. The data show that culture in the presence of isolated protein complexes in the absence of serum consistently achieved at least 90% of the cell growth achieved in the presence of 10% serum.

Figure 2:
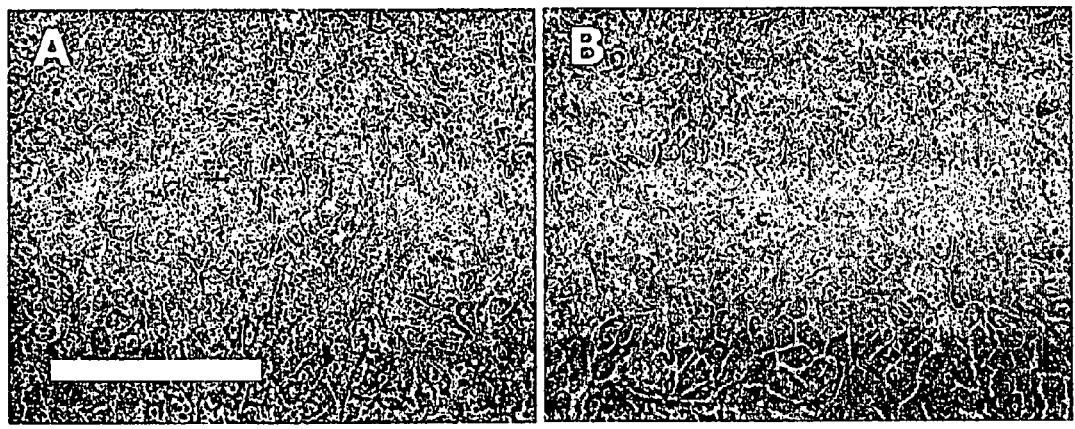

Referring to FIGS. 2A and 2B, skin cells grown on Vitro-Gro display a similar appearance to those grown in the presence of fetal bovine serum (FIG. 2A). A more detailed comparison based on the presence of molecular markers is currently in progress to confirm this conclusion. Techniques employed will include immunocytochemistry, fluorescence activated cell sorting (FACS) analysis, western blotting, and polymerase chain reaction (PCR) methods. The use of state-of-the-art proteonomic and gene array technologies are also being considered. Major markers for investigation will include cytokeratins (CK1 and CK10, CK6, CK14, and CK19) and putative keratinocyte progenitor cell markers (e.g. p63, α9-integrin, α6-integrin$^{bri}$/CD71$^{dim}$). Particular attention will be placed on comparing the expression of putative progenitor cell markers since these are likely to confer clinical efficacy in cultures following grafting. In addition, the responses of cells in routine in vitro functional assays may also be performed (attachment, migration, proliferation).

Relative Activity of Isolated Protein Complexes Containing IGFBP3 or IGFBP5

Referring to FIG. 3, it is apparent that isolated protein complexes comprising IGFBP5 were more efficient than IGFBP3-containing complexes in terms of keratinocyte yield.

Example 2

Primary Human Keratinocyte Growth in the Absence of Serum with and without Feeder Cells Materials and Methods Primary Keratinocyte Culture Keratinocytes were isolated from adult human skin using the standard procedures essentially the same as that originally reported by Rheinwald & Green, 1977, Nature 265 421. Briefly this involved digestion of the skin sample for one hour at 37° C. in Dispase II solution. The recovered epithelium is subsequently digested for a further 10 minutes at 37° C. with 0.25% trypsin/0.02% EDTA to dissociate the cells. Residual trypsin activity is inactivated and recovered cells are then washed and co-seeded into tissue culture dishes in the presence or absence of lethally irradiated 3T3 mouse fibroblasts. "Control" cells, cultivated using these standard conditions are grown in DMEM/F12 medium supplemented with 10% fetal calf serum, 0.1% penicillin-streptomycin solution, 0.4 µg/ml hydrocortisone, 0.1 µg/ml cholera toxin, 10 ng/ml human recombinant epidermal growth factor (EGF), 5 µg/ml insulin, 5 µg/ml transferrin and 2 nM tri-iodothyronine, while cells treated with isolated growth factor complexes used identical media except that no insulin was present. Insulin was not included in media used in conjunction with isolated protein complex treatments to minimize competitive binding of insulin to the type-1 IGF receptor. Cells cultured on isolated growth factor complex-coated dishes also differed from those cultured following the standard procedure in that the cells will be seeded onto plates without irradiated mouse fibroblasts.

Protein Synthesis Assay

Keratinocytes were derived from an adult skin biopsy and expanded until passage 2 using standard procedures incorporating Greens media, serum and feeder cells. These cells were then assessed for the stimulation of protein synthesis in the presence and absence of IGF+VN complexes. Here, 24 well plates were coated for 2 hours with 300 ng of vitronectin and then washed to remove unbound vitronectin. Wells were then incubated with the growth factors to be examined, that is; epidermal growth factor, basic fibroblast growth factor, insulin-like growth factor-I and insulin-like growth factor-II, in combination with insulin-like growth factor binding protein-5; were added to the wells and allowed to bind the vitronectin overnight. The next day the wells were washed twice to remove any unbound growth factors and the plates allowed to air dry. Keratinocytes were then harvested and seeded at a density of $1 \times 10^5$ cells/well in serum-free Dulbecco's Modified Eagle Medium (DMEM) along with 1 uCi/well of [$^3$H]-leucine. In select wells, cells were seeded in Defined Keratinocyte Medium (DKM) (Invitrogen), a commercially available product for the serum-free culture of keratinocytes. Plates were then incubated for 48 hours and then washed to remove any unincorporated [$^3$H]-leucine. Incorporation of [$^3$H]-leucine into de novo synthesised protein was determined by sampling solubilised protein precipitate for beta-scintillation counting.

MTT-Esta Assay

Human keratinocytes were isolated and the cultures established using standard culture techniques of fully supplemented Greens Media with a feeder layer of lethally irradiated mouse 3T3 cells. Cells were expanded to passage 3 and seeded into 24 well plates in Greens media in the presence or absence of Fetal Calf Serum (FCS) and 3T3 cells. In select treatments, wells were coated with isolated protein complexes. Wells were incubated with 300 ng of vitronectin for 2 hours and then aspirated prior to the addition of IGF-I and IGFBP3 or IGFBP5, or IGF-II. Plates were incubated overnight and aspirated prior to seeding cells. The cultures were assessed for metabolic activity as measured using the MTT-esta assay as described previously (Ealey et al. 1988, J Mol Endocrinol 1:R1-R4.).

Results

In view of the significant enhanced functional responses obtained with isolated growth factor complexes in cell lines (International Publication WO 02/24219; Noble et al., 2003, supra; Kricker et al., 2003, supra) we recently extended our studies to cultures of keratinocytes derived from adult skin. In particular we examined the potential of isolated growth factor complexes to replace serum and feeder cells used in current best clinical practice for ex vivo expansion of keratinocytes for split thickness autografting. While this procedure has significantly advanced therapies available to burns patients, the culture of keratinocytes derived from patients is conducted in the presence of fetal bovine serum (FBS), a semi-defined xenobiotic product that is a potential source of pathogens. In addition, in the early stages of keratinocyte derivation and establishment a feeder layer of cells derived from a second species, namely murine 3T3 fibroblasts, is used as a source of cytokines and matrix elements to encourage cell attachment and growth. FBS also contributes to these effects.

As (i) IGFs account for a large proportion of the cytokines secreted by the feeder cells; (ii) we have established that VN replaces any requirement for serum to facilitate the attachment of primary cultured keratinocytes seeded at low density to plasticware; and iii) the effects we have obtained with keratinocyte cell lines cultured on isolated growth factor complexes are equivalent to those obtained with media containing 10% FBS, we hypothesised that isolated growth factor complex-supplemented media had the potential to provide a superior product for autologous keratinocyte engineering applications. This hypothesis is supported by the fact that IGFs are key mitogens that stimulate keratinocyte proliferation, yet keratinocytes themselves do not secrete IGF-I. While serum-free media, such as KGM™ (Clonetics) and EpiLife™ (Sigma-Aldrich), have been developed commercially for keratinocyte expansion, these media require the addition of bovine pituitary extract, which is also undefined, a xenobiotic and a potential source of pathogens, or alternatively, the addition of expensive supplements. Furthermore, most current serum-free keratinocyte culture applications demand very high seeding densities which defeats the purpose of attempting to culture large quantities of keratinocytes rapidly and accounts for the poor adoption of these practices for routine clinical applications.

We have directly tested our hypothesis and the results are illustrated in FIG. 4. In this experiment keratinocytes were derived from adult skin and established using usual procedures for 7 days. The cells were then passaged by trypsinisation and seeded at low density (8,500 keratinocytes/cm$^2$) on isolated growth factor complex-coated tissue culture plastic and grown in the absence of feeder cells, and minus both FBS and insulin (FIG. 4) for a further 7 days. Cells grown in these conditions were found to expand more rapidly than those grown using only current best clinical practice (i.e. grown in the presence of FBS and 3T3 mouse feeder fibroblasts; FIG. 4). The margins of the colony grown in the presence of isolated protein complexes demonstrate keratinocytes that are outwardly mobile, healthy and proliferating. The innermost cells depicted in FIG. 4 show the typical pavement morphology observed in keratinocyte cultures near confluence, with confluence in this case obtained in just 7 days. Quantification of keratinocyte proliferation in the presence of these protein complexes via MT assay confirms these findings (FIG. 4B).

Subsequent data has tended to suggest that the ability of keratinocytes to grow well in the absence of feeder cells (also without serum) is restricted to later stages of cell culture as feeder cells appear to be important for the establishment of the cultures from the initial biopsies.

The effect of additional growth factors EGF and bFGF is demonstrated in FIG. 5. We examined passage 3 human skin keratinocytes (derived from an adult skin biopsy) and assessed the stimulation of protein synthesis by supplemented IGF+VN complexes over 48 hr. These treatments were tested in parallel with cells grown in Defined Keratinoctye-SFM (DKM) (Invitrogen), a commercially available product for the serum free culture of keratinocytes, containing undefined amounts of insulin, EGF and bFGF. DKM was found to stimulate increases in protein synthesis of 148% above control wells (−VN), which was significantly higher ($p<0.05$) than the effect of VN alone (+VN) or the absence of VN and growth factors (−VN). The dimeric IGF-II+VN and trimeric IGF-II+VN+IGFBP-5 complexes also stimulated significant increases in protein synthesis of 134% and 161% respectively ($p<0.05$). Indeed there were no significant differences ($p>0.05$) in the stimulation of protein synthesis observed for DKM, dimeric and trimeric complexes, indicating that both complexes are equally efficient at stimulating keratinocyte protein synthesis as the commercially available DKM.

When EGF, bFGF, or both growth factors in combination, were added to the trimeric complex increases of 216%, 248% and 213% were observed. AU of these responses were significantly higher than that of DKM ($p<0.05$). Likewise, when EGF, or both EGF and bFGF, were added to dimeric complexes, significant increases in protein synthesis of 192% and 198% respectively, were obtained which were also significantly higher than that of DKM ($p<0.05$). These results highlight that incorporating EGF and bFGF into isolated protein complexes stimulate increases in protein synthesis above that of a commercially available product for the serum-free and feeder-free cultivation of keratinocytes.

Example 3

Skin Spray Technology

Materials and Methods

There are two issues addressed here. First, sufficient numbers of cells are produced on VitroGro to support application of sprayed cell suspensions within one week. This technique is therefore consistent with that already used commercially (Clinical Cell Culture Ltd), but has the advantage of being serum-free. Secondly, cells grown on VitroGro remain viable following spraying. The delivery system that we have used is Tissomat® (Baxter Healthcare). The Tissomat delivery system is designed for the spray-application of fibrin glue and aerosolises liquids via delivery into a stream of compressed medical grade air controlled by a regulator. Nevertheless, it is also our expectation that similar results can be achieved using alternative spray methods (syringe fitted with spray cap). Pressures of between 10-30 psi are suitable, but a drop in viability is observed within increasing pressure. Cells may be sprayed at concentrations of between 0.5 to 1.5 million per milliliter. Application of 0.2 milliliters of cell suspension at 20 psi is sufficient to cover an area of approximately 25 square centimeters (based on measurement of surface area covered with cells after 7 days growth in vitro). Cells can be delivered in serum free growth medium, but may also be suspended in fibrin glue such as the commercially available Tisseel/Tissucol (Baxter Healthcare). Our studies indicate that fibrin glue should be adjusted prior to use by diluting to isotonic conditions with sterile water for injection and further adjusting the final fibrin glue components with sterile saline to between 1-10 mg/ml for fibrinogen and between 10-100 Units/ml for Thrombin.

Results

FIG. 6 demonstrates cell distribution and growth following spray delivery of keratinocytes into 150 mm diameter collagen-coated cultures dishes. Importantly, cells grown on VitroGro display good viability following being sprayed. Cells were sprayed at two different concentrations to determine cell numbers required to cover sprayed area. The cultures used for spraying were originally grown on either control (with serum), vitronectin with IGFBP3 and IGF-I. All cultures were prepared in the presence of 3t3 cells. Following spraying, the cells have been grown in the presence of serum to mimic conditions that are likely to be experienced on the wound bed. The cultures have been stained with crystal violet to demonstrate the cellular distribution.

As shown in FIG. 7, the effects of spraying cultured keratinocytes with the Tissomat delivery system can be seen. For these preliminary experiments, cultures were established using the conventional culture medium with added serum and feeder cells. In FIG. 7A, the Trypan Blue exclusion test was performed within minutes following spraying cells into a collection tube and works on the principle that viable cells are not permeable to the dye. As can be seen in FIG. 7B, the MT conversion data is a more robust measure of viability as it provides an indication of the metabolic activity 24-hours after spraying the cells.

In both FIGS. 7A and 7B, it can be seen that an optimal delivery pressure is 10-20 psi, although viability is still acceptable at a delivery pressure of 30 psi.

Example 4

Skinspray Clinical Trial

Harvesting of Skin Biopsy

A suitable donor site will be selected and prepped by shaving and swabbing with disinfectant. A split thickness skin graft of approximately 10 square centimeters in area will be removed in theatre under local anesthetic. The biopsy will be placed in sterile saline solution with antibiotics and immediately transported to the skin culture laboratory for processing. The donor site will be dressed with Opsite or other dressing according to the judgement of the attending surgeon.

Isolation and Culturing of Keratinocytes

Upon arrival at the skin culture facility, each patient biopsy will be washed in sterile buffer and incubated for 1 hour at room temperature in antibiotics to reduce the likelihood of contamination during subsequent culture. The epidermal and dermal layers will be separated by digestion with trypsin. The opposing faces of the separated tissue will be scraped and the dislodged cells (predominantly basal keratinocytes) washed and resuspended in serum-free medium containing soybean trypsin inhibitor. The final cell suspension will be seeded into a 25 cm$^2$ tissue culture flask containing growth arrested mouse 3t3 fibroblasts ($2.5\times10^4$/cm$^2$) and 5 ml of DMEM/F12 culture medium supplemented with vitronectin (VN, 50 ng/cm$^2$), insulin-like growth factor I (IGF-I, 15 ng/cm$^2$), insulin-like growth factor binding protein 5 (IGFBP5, 50 ng/cm$^2$), epidermal growth factor (EGF, 15 ng/cm$^2$), adenine (180 μM, cholera toxin (0.1 μg/ml), L-glutamine (2 mM), hydrocortisone (0.4 μg/ml) and non-essential amino acids (1% v/v). Culture flasks will be pre-treated with VN (300 ng/cm$^2$), IGF-I (100 ng/cm$^2$), IGFBP5 (500 ng/cm$^2$) and EGF (100 ng/cm$^2$) to promote pre-absorption of protein complexes. Fresh medium will be applied after 3 days culture. After 6 days culture, the 3t3 cells will be removed by incubating in buffered saline containing EDTA. The remaining keratinocytes will be harvested by further incubation with Trypsin/EDTA and washed in buffered saline containing soybean trypsin inhibitor. Recovered cells will be adjusted to a concentration of 2×10$^6$/ml and transported to the operating theatre in buffered saline containing 0.2% human serum albumin.

Preparation and Delivery of Keratinocyte Suspension

The TISSEEL Duo 500® will be thawed according to manufacturers instructions by placing at 37° C. Once thawed, the fibrinogen and thrombin syringes will be removed from their respective holders and dispensed into sterile plastic tubes. The fibrinogen component will be diluted 1:1 with sterile water for injection followed by a further 1:4 dilution with the stock patient cell suspension (2×10$^6$ cells/ml, as prepared in step 2). The thrombin component will be diluted 1:0.25 (i.e 4:1) with sterile water for injection. An equal volume of each modified component (fibrinogen+cells, and thrombin) will be loaded into separate 1 ml syringes and attached to TISSOMAT via a Duploject spray nozzle. During application, the two syringes will be uniformly depressed resulting in a further 1:1 mixture of each component. Thus, the final concentrations will be: 0.8×10$^6$ cells/ml, 170 IU/ml Thrombin, and 4.7 mg/ml fibrinogen in the sprayed product. Approximately 0.5 ml of combined solution will be sequentially delivered from a height of 10 cm at 20 psi to each 20 cm$^2$ of split thickness wound. Thus the average seeding density of applied cells will be 0.2×10$^5$/cm$^2$. The height and interval for each spray will be approximated using hand width (height) and the combined width of three fingers (interval). The treated wounds will be created in the course of performing a routine split thickness autograft (treatment of burns or contracture releases). Approximately half of each wound will be covered with a sterile mask during spraying to serve as a non-treated control. Two donor sites may be used: one treated and one left untreated. Each wound will be photographed both prior and after applying the cell suspension. Treated wounds will be covered with Opsite silicone dressing.

Post-operative clinical care and assessment will be undertaken according to established protocols.

Example 5

Growth and Migration of ORS-Derived Cells

Primary outer root sheath (ORS) cultures will be derived from anagen-phase hair follicles harvested from the scalp of consenting diabetic patients and cultured using the methods described by Limat & Hunziker, 2002, Cells Tissues Organs 172 79-85 and International Publication WO 01/59442. The cells will be ex vivo expanded using a pre-formed feeder layer of post-mitotic human dermal fibroblasts and fetal calf serum supplemented media as described above for keratinocytes derived from skin. The cultures will be maintained in a subconfluent state for a maximum of three passages and morphological and functional assessment of the growth of the cells in the presence of isolated protein complexes examined in the absence of serum and feeder cells.

The particular complexes determined to be optimal for skin-derived keratinocyte growth will be tested.

Having established that ex vivo expanded ORS-derived keratinocyte progenitor cells grow and migrate in the presence of isolated protein complexes, it will then be determined whether the initial derivation of the cells from the anagen-phase ORS and the subsequent primary culture can also be performed in serum- and feeder cell-free conditions. Thus the ORS of anagen-phase follicles will be explanted onto the microporous membranes of cell culture inserts and rather than coating the underside of the membrane inserts with a feeder layer of postmitotic dermal fibroblasts, the undersurface will instead be coated with isolated protein complexes. The cells will be grown in serum-free media alone, or media supplemented with autologous serum obtained from the patient, or media containing isolated protein complexes. The growth rate of the ORS-derived cells grown the presence of isoolated protein complexes will be compared with cells grown on inserts using standard procedures.

Epidermal equivalents will also be prepared by exposing the cells to air, as described by Limat & Hunziker, 2002, supra, and characterized using histological, ultrastructural (e.g. basement membrane-like structure, keratohyalin granules, keratinosomes) and immunohisto-chemical (e.g. keratins, integrins, gp80, involucrin, filaggrin) criteria. If successful, use of ORS-derived progenitor cells with this growth factor+VN technology will not only significantly reduce manufacturing costs, but will also enhance safety, thus expedite regulatory issues associated with the approval of a cell-based therapeutic.

Example 6

Preparation of Purified Vitronectin

Autologous VN purified patient blood (typically present at 0.4 mg/ml) will be used to support the growth of the patient's own keratinocytes ex vivo. We will evaluate monoclonal antibodies produced against vitronectin and that have successfully been used for purification of vitronectin from human serum (Underwood et al., 2001, J Immunol Methods. 247 217-24). The monoclonal antibodies selected for evaluation will be coupled to the support purification matrix using methodologies similar to those described by to purify VN from serum. At this stage we estimate we will need 0.25 mg of VN to culture 1 m$^2$ of patient cells and this should be readily obtained from 20 ml of patient blood. The purification procedure by Underwood et al., 2001, supra will be modified with the emphasis being on minimal manipulation and simplicity the aim being to develop a disposable affinity purification matrix that requires ideally, only 2-3 washing steps. As the VN will be from the patients themselves, the requirement for pure VN is reduced, provided that the VN obtained is able to still promote cell growth efficiently. Thus VN purified using the protocols developed will be evaluated for efficacy in promoting keratinocyte growth as well as through standard biochemical analyses such as SDS-PAGE, N-terminal protein sequencing, electrospray mass analysis, IGF- and IGFBP-binding, and will be compared with VN purchased from Promega Pty. Ltd.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:

1. A mammalian cell culture medium comprising:
   (i) a synthetic, chimeric oligo-protein complex comprising a fused contiguous sequence of amino acids comprising:
   (a) insulin-like growth factor I (IGF-I), and
   (b) an $\alpha_v$ integrin-receptor binding domain of vitronectin (VN), wherein the binding domain does not comprise a heparin binding domain (HBD); and
   wherein the synthetic, chimeric oligo-protein complex does not comprise an insulin-like growth factor binding protein (IGFBP); and
   (ii) an absence of serum or an amount of serum which would not support cell growth when said IGF-I is not present.

2. The mammalian cell culture medium of claim 1, wherein the serum is absent or present at a concentration no more than 1% (v/v).

3. The mammalian cell culture medium of claim 2, wherein the serum is absent or present at a concentration no more than 0.5% (v/v).

4. The mammalian cell culture medium of claim 3, wherein serum is present at a concentration no more than 0.1% (v/v).

5. The mammalian cell culture medium of claim 1, wherein serum is absent.

6. The mammalian cell culture medium of claim 1, further comprising an IGFBP selected from the group consisting of IGFBP1, IGFBP2, IGFBP3, IGFBP4, IGFBP5 and IGFBP6.

7. The mammalian cell culture medium of claim 6, wherein the IGFBP is selected from the group consisting of IGFBP3 and IGFBP5.

8. The mammalian cell culture medium of claim 7, wherein the IGFBP is IGFBP5.

9. The mammalian cell culture medium of claim 1, wherein the $\alpha_v$ integrin-receptor binding domain of VN comprises a polyanionic region.

10. The mammalian cell culture medium of claim 1, wherein the $\alpha_v$ integrin-receptor binding domain of vitronectin (VN) is capable of non-covalent binding to an integrin receptor selected from $\alpha_v\beta_3$ integrin receptor or an $\alpha_v\beta_5$ integrin receptor.

11. The mammalian cell culture medium of claim 1, wherein the synthetic chimeric oligo-protein complex is a recombinant oligo-protein complex.

12. The mammalian cell culture medium of claim 1, further comprising one or more other biologically active proteins that promote cell growth and/or differentiation.

13. The mammalian cell culture medium of claim 12, wherein said one or more other biologically active proteins is EGF and/or bFGF.

14. A composition comprising the mammalian cell culture medium of claim 1 and further comprising epithelial cells.

15. A cell culture vessel comprising the mammalian cell culture medium of claim 1.

16. The cell culture vessel of claim 15, wherein the $\alpha_v$ integrin-receptor binding domain of VN is immobilized, bound, or otherwise associated with the culture vessel.

17. The composition of claim 14, wherein said epithelial cells are keratinocytes.

* * * * *